United States Patent

Augustijn et al.

(10) Patent No.: US 7,369,891 B2
(45) Date of Patent: May 6, 2008

(54) RATE CONTROL TECHNIQUES FOR IMPLANTABLE PULSE GENERATOR SYSTEMS

(75) Inventors: Frederik Augustijn, Arnhem (NL); Johannes Simon van der Veen, Dieren (NL); Lucas Johannes José Marie Meekes, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 483 days.

(21) Appl. No.: 10/422,079

(22) Filed: Apr. 23, 2003

(65) Prior Publication Data

US 2004/0215250 A1  Oct. 28, 2004

(51) Int. Cl.
*A61N 1/368* (2006.01)
(52) U.S. Cl. ............................................. 607/9
(58) Field of Classification Search ................ 607/9, 607/14, 15
See application file for complete search history.

(56) References Cited

U.S. PATENT DOCUMENTS

| 4,250,884 | A |  | 2/1981 | Hartlaub et al. |  |
|---|---|---|---|---|---|
| 4,266,551 | A |  | 5/1981 | Stein |  |
| 4,515,159 | A |  | 5/1985 | McDonald et al. |  |
| 4,554,922 | A | * | 11/1985 | Prystowsky et al. | 607/14 |
| 6,078,837 | A | * | 6/2000 | Peterson et al. | 607/14 |
| 7,003,347 | B2 | * | 2/2006 | Stahmann | 607/9 |
| 2001/0012953 | A1 | * | 8/2001 | Molin et al. | 607/9 |

* cited by examiner

*Primary Examiner*—Angela D. Sykes
*Assistant Examiner*—Michael Kahelin
(74) *Attorney, Agent, or Firm*—Daniel G. Chapik (57) ABSTRACT

The invention is directed to rate control techniques for implantable pulse generator (IPG) systems. The techniques make use of a plurality of timing intervals that may replace conventional rate control and allow "double-pacing" pulses to be delivered in certain instances. For example, a second pulse, i.e., a "double-pacing" pulse, may delivered within a first time interval relative to delivery of the first pulse. However, the second pulse is not allowed once the first time interval has elapsed, if a second time interval has not also elapsed. If the second pulse is delivered during the first time interval, then the second time interval is restarted and another pulse cannot be delivered until the restarted second time interval has elapsed.

13 Claims, 7 Drawing Sheets

RATE CONTROL TECHNIQUES FOR IMPLANTABLE PULSE GENERATOR SYSTEMS

FIELD OF THE INVENTION

The invention relates to implantable medical devices, and more particularly to implantable pulse generator (IPG) systems that deliver therapeutic stimulation pulses to a patient.

BACKGROUND OF THE INVENTION

A wide variety of medical devices have been developed for delivery of stimulation therapy to a patient. An implantable pulse generator (IPG) system generally refers to such a medical device that delivers pulses of therapeutic stimulation. IPG systems include an IPG device and one or more implantable medical leads coupled to the IPG device. The IPG device comprises a housing that houses circuitry for the generation of the therapeutic stimulation pulses, and the leads position electrodes within the patient at locations desirable for delivery of such pulses. The IPG device is typically a biocompatible hermetically sealed structure that, like the leads, is implanted in the patient. However, in some cases, only the leads are implanted, and the IPG device resides at a location external to the patient.

One common example of an IPG device is a pacemaker. A pacemaker system typically includes a pacemaker device and one or more pacing and sensing leads for delivery of pacing pulses to a patient's heart. Another example of an IPG device is a combination pacemaker-cardioverter-defibrillator. Other examples include implantable brain stimulators, implantable gastric system stimulators, implantable nerve stimulators or muscle stimulators, implantable lower colon stimulators, and so on.

Rate control of the delivery of stimulation pulses is of paramount concern in pacemaker systems and other IPG systems. For example, stimulation of a patient's ventricles typically should not exceed 200 paces per minute. Conventionally, stimulation of the ventricles at rates above 200 paces per minute is considered very dangerous, and is sometimes considered potentially lethal. For this reason, pacemaker systems typically implement some type of rate control algorithm that limits the rate at which ventricular pacing pulses can be delivered. For example, the pacemaker may limit the ability to deliver another ventricular pacing pulse within a 300 millisecond time interval following the delivery of an earlier ventricular pacing pulse. In this manner, the pacemaker can ensure that stimulation of a patient's ventricles will never exceed 200 paces per minute.

BRIEF SUMMARY OF THE INVENTION

In general, the invention is directed to rate control techniques for implantable pulse generator (IPG) systems. The techniques make use of a plurality of timing intervals that may replace conventional rate control and allow "double-pacing" pulses to be delivered in certain instances, such as when the first pacing pulse does not achieve capture or when double-pacing pulses are applied for cardiac resynchronization. A first time interval is referred to as a double-pace window and may span approximately 100 milliseconds or less. The second timing interval is referred to as a rate control window and may span approximately 300 milliseconds, similar to conventional intervals that limit the ability to deliver another ventricular pacing pulse within the 300 milliseconds.

In accordance with the invention, a second pulse, i.e., a "double-pacing" pulse, may be delivered within the first time interval. However, the second pulse is not allowed once the first time interval has elapsed, if the second time interval has not also elapsed. If the second pulse is delivered during the first time interval, then the second time interval is restarted and another pulse cannot be delivered until the restarted second time interval has elapsed, e.g., 300 milliseconds following delivery of the second pacing pulse.

In one embodiment, the invention provides an implantable pulse generator system comprising an implantable pulse generator device and one or more implantable leads coupled to the implantable pulse generator device to position one or more electrodes within a patient. The system may include circuitry to deliver therapeutic pulses to the patient via the electrodes, and a rate control unit to define first and second time intervals relative to a first stimulation pulse delivered to the patient, the first time interval being shorter than the second time interval, allow delivery of a second stimulation pulse during the first time interval, and disallow delivery of the second stimulation pulse following the first time interval during the second time interval.

In another embodiment, the invention provides a method comprising delivering a first stimulation pulse to a patient and defining first and second time intervals relative to the first stimulation pulse, the first time interval being shorter than the second time interval. The method may further comprise allowing delivery of a second stimulation pulse during the first time interval, and disallowing delivery of the second stimulation pulse following the first time interval during the second time interval.

In another embodiment, the invention provides a circuit for an implantable pulse generator. The circuit can be configured to deliver a first stimulation pulse to a patient, define first and second time intervals relative to the first stimulation pulse, the first time interval being shorter than the second time interval, allow delivery of a second stimulation pulse during the first time interval, and disallow delivery of the second stimulation pulse following the first time interval during the second time interval.

In another embodiment, the invention may be implemented in software. In that case, the invention provides a computer readable medium comprising computer readable instructions that when executed in an implantable pulse generator cause the implantable pulse generator to define first and second time intervals relative to a first stimulation pulse delivered to a patient, the first time interval being shorter than the second time interval, allow delivery of a second stimulation pulse during the first time interval, and disallow delivery of the second stimulation pulse following the first time interval during the second time interval.

In another embodiment, the invention provides an apparatus comprising means for delivering a first stimulation pulse to a patient, means for defining first and second time intervals relative to the first stimulation pulse, the first time interval being shorter than the second time interval, means for allowing delivery of a second stimulation pulse during the first time interval, and means for disallowing delivery of the second stimulation pulse following the first time interval during the second time interval.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The invention is directed to rate control techniques for implantable pulse generator (IPG) systems. The techniques make use of a plurality of timing intervals to improve rate control and allow "double-pacing" pulses to be delivered in certain instances, such as when the first pacing pulse does not achieve capture or when double-pacing pulses are applied for cardiac resynchronization. A first time interval is referred to as a double-pace window and may span approximately 100 milliseconds or less. The second timing interval is referred to as a rate control window and may span approximately 300 milliseconds, similar to conventional intervals that limit the ability to deliver two ventricular pacing pulses within the 300 milliseconds.

In accordance with the invention, a second pulse, i.e., a "double-pacing" pulse, may be delivered within the first time interval relative to delivery of a first pulse. However, the second pulse is not allowed once the first time interval has elapsed, if the second time interval has not also elapsed. In other words, the second pacing pulse is only allowed during the first time interval, e.g., within 100 milliseconds of the first pacing pulse. After the first time interval elapses, additional pulses are not allowed until the second time interval elapses. At that point, the process repeats.

For example, if the first interval is 100 milliseconds and the second interval is 300 milliseconds, a second "double pacing" pulse is allowed only if it occurs within 100 milliseconds of the first pulse. In that case, the second pulse is not allowed after the 100 milliseconds have elapsed and before 300 milliseconds have elapsed. In other words, the second pulse is not allowed to occur between 100 and 300 milliseconds of the first pacing pulse. The period between 100 and 300 milliseconds of the first pacing pulse can be referred to as a vulnerable period during which delivery of pacing pulses could invoke fibrillation or possibly death. Once the 300 milliseconds have elapsed, any pacing pulse is allowed and the process repeats.

If the second pulse, i.e. the "double pacing" pulse, is delivered during the first time interval, then the second time interval is restarted relative to the second pulse. In that case, another pulse generally cannot be delivered until the restarted second time interval has elapsed. For example, if the first interval is 100 milliseconds and the second interval is 300 milliseconds, and a second "double pacing" pulse is delivered within the 100 milliseconds of the first pulse, then the second interval of 300 milliseconds is restarted relative to delivery of the second pacing pulse. Thus, no additional pacing pulses are allowed for 300 milliseconds following delivery of the second pacing pulse. In other embodiments, however, additional "triple-pacing" pulse windows, or the like, may be defined as well.

Figure 1:
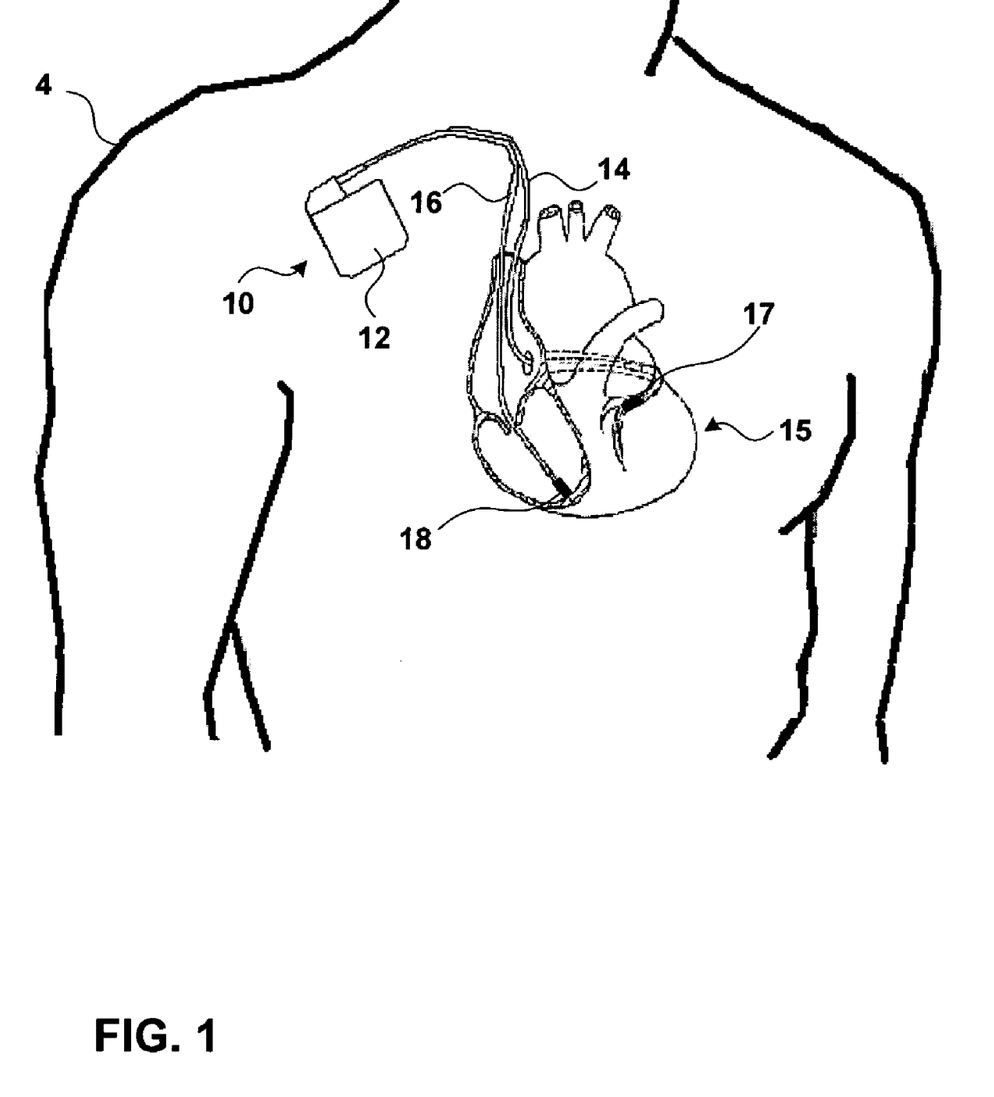
FIG. 1 is a schematic view of an implantable pulse generator (IPG) system implanted within a human.

FIG. 1 is a simplified schematic view of pacemaker system 10 within a patient's body 4. Pacemaker system 10 represents one embodiment of an implantable pulse generator (IPG) system according to the invention. Pacemaker system 10 includes a pacemaker device 12, and one or more pacing and sensing leads 14 and 16 coupled to pacemaker device. Leads 14, 16 each position one or more electrodes 17, 18 with respect to heart 15. Electrodes 17, 18 sense electrical signals attendant to the depolarization and repolarization of heart 15, and deliver pacing pulses generated by pacemaker device 12 for causing depolarization of cardiac tissue in the vicinity of the respective electrode 17, 18. Electrodes 17, 18 may comprise unipolar or bipolar electrodes, as are well known in the art. Although FIG. 1 illustrates leads being positioned in the ventricles, it is understood that the invention may be practiced in pacemaker systems having any number of leads. For example, in some cases, the invention can be practiced in pacemaker systems having a single ventricular lead with one or more electrodes.

Implantable leads 14, 16 may include any number of additional electrodes (not shown) distributed along the length of the respective lead. Electrodes 17, 18 or other electrodes may be used for sensing and/or delivery of stimulation pulses. Additional electrodes (not shown) may also be used for delivery of high voltage defibrillation or cardioversion shocks.

Electrodes 17, 18 can be made from an electrically conductive, biocompatible material such as elgiloy, platinum, platinum-iridium, platinum-iridium oxide, sintered platinum powder or other residue product after combustion with some high heat source, platinum coated with titanium-nitride, pyrolytic carbon, or the like. Electrodes 17, 18 are electrically coupled to one or more conductive filars that extend along the body of the respective lead 14, 16, e.g., in a coiled construction. Although two leads 14, 16 are shown for purposes of illustration, any number of leads may be used in system 10.

Electrodes 17, 18 may form a substantially cylindrical ring of conductive material that extends about an exterior wall of leads 14, 16. For example, electrodes 17, 18 may extend the entire 360 degrees about leads 14, 16, or to some lesser extent. In some embodiments, leads 14, 16 may be tubular but not necessarily cylindrical. For example, electrodes 17, 18 and leads 14, 16 may have alternative cross sections, e.g., square, rectangular, hexagonal, oval or the like. In any case, electrodes 17, 18 can be coupled to one or more electrically conductive filars that extend along the length of leads 14, 16. The filars are typically coiled to define a lumen of the respective lead 14, 16.

Many details of the invention will be provided in the context of a pacemaker system 10, which may comprise an implantable cardiac pacemaker, a combination pacemaker-cardioverter-defibrillator, or the like. The invention, however, is not limited for use with cardiac pacing, but may find wide applicability with any IPG that delivers therapeutic pulses to any location within a patient. For example, the invention may find use with a neurological device such as a deep-brain stimulation device or a spinal cord stimulation device. In those cases, the leads may be stereotactically probed into the brain to position electrodes for deep brain stimulation, or into the spine for spinal stimulation. In other applications, invention may be used with muscular stimulation devices, gastric system stimulation devices, nerve stimulation devices, lower colon stimulation devices, or the like. In short, rate controlled pacing techniques, described herein, may find useful applications in a wide variety IPG systems. For purposes of example, in the description that follows, rate control techniques are described as being applied to a patient's heart, e.g., for cardiac pacing.

Figure 2:
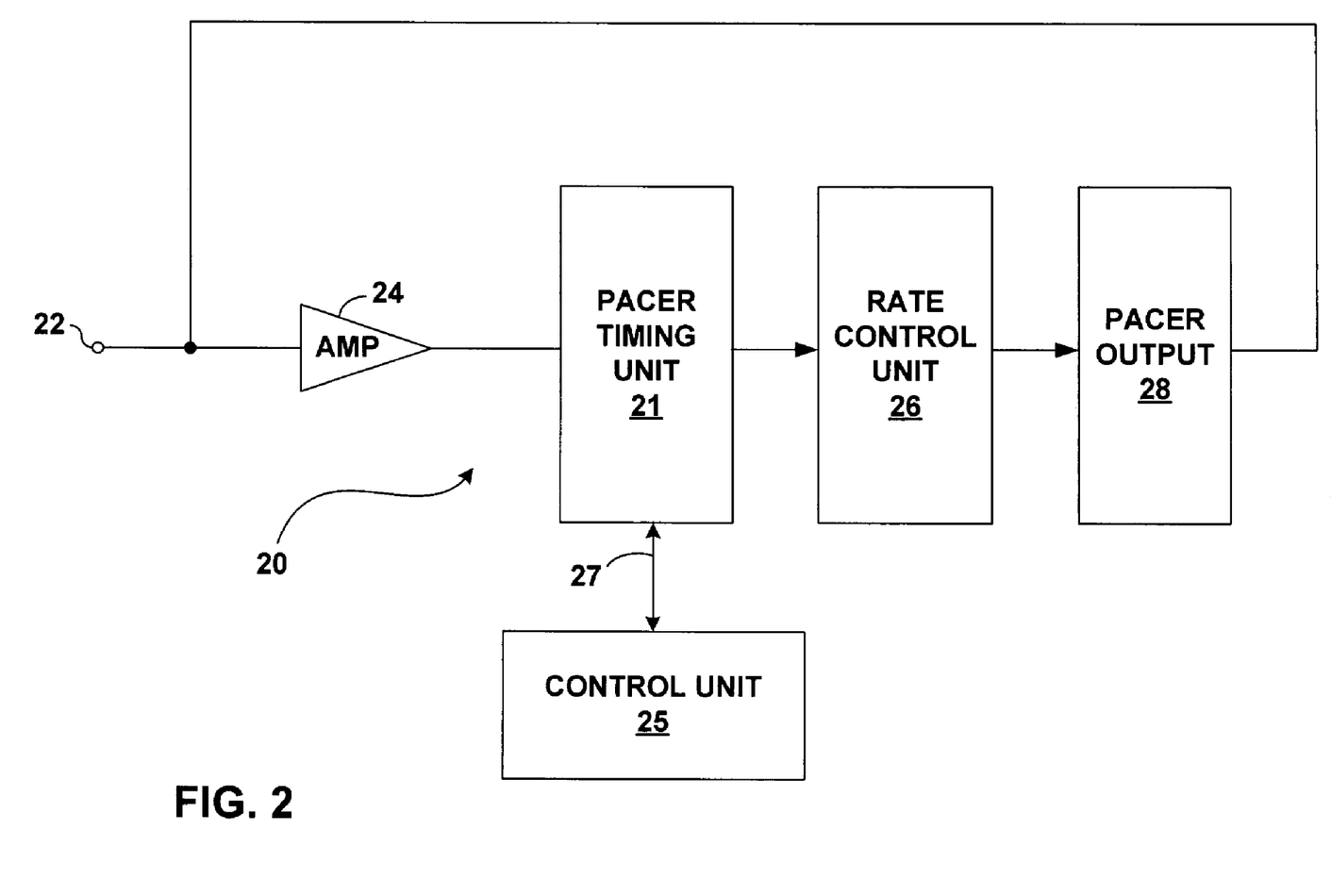
FIG. 2 is a block diagram of an exemplary IPG system in the form of a cardiac pacemaker.

FIG. 2 is a simplified block diagram of an exemplary IPG system 20 in the form of a cardiac pacemaker. System 20 may correspond to system 10 of FIG. 1. In general, IPG system 20 comprises an IPG device that includes the various circuitry components illustrated in FIG. 2 and one or more leads (not illustrated) coupled to the circuitry to position an electrode 22 within the patient's heart. Electrode 22 may comprise a unipolar or bipolar electrode design.

Figure 6:
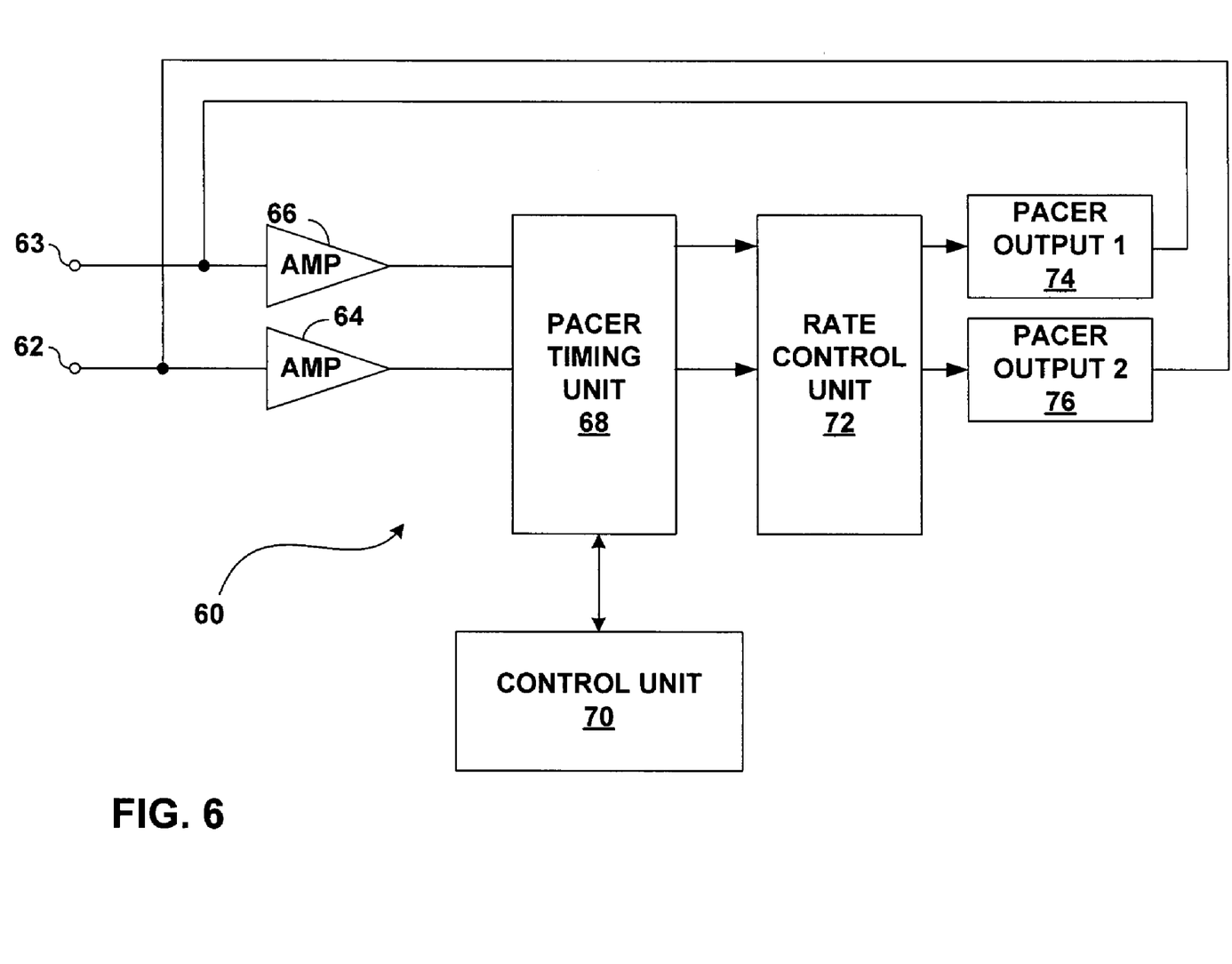
FIG. 6 is another block diagram of an exemplary IPG system in the form of a cardiac pacemaker that includes two or more electrodes.

In general, pacer timing unit 21 controls the timing of delivery of pacing pulses at the direction of control unit 25. For example, control unit 25 may execute a pacing algorithm and direct pacer timing unit 21 to time pacing pulses based on conditions sensed by electrode 22. Pacer timing unit 21 may include programmable digital counters which control the basic time intervals associated with modes of pacing. Pacer timing unit 21 may also control escape intervals associated with pacing. Although not illustrated in FIG. 2, system 20 may include additional electrodes, e.g., for bi-ventricular pacing. FIG. 6 illustrates one configuration that may correspond to a bi-ventricular pacing environment and is described in greater detail below.

Referring again to FIG. 2, intervals defined by pacer timing unit 21 may also include atrial pacing escape intervals, the refractory periods during which sensed P-waves and R-waves are ineffective to restart timing of the escape intervals and the pulse widths of the pacing pulses. The durations of these intervals may be determined by control unit 25, which can comprise a microprocessor coupled to a memory device (not shown). In some cases, control unit 25 may also determine the amplitude of the cardiac pacing pulses and send control signals to pacer output unit 28 in order to cause pacer output unit 28 to generate the desired amplitude of pacing pulses.

During pacing, escape interval counters within pacer timing unit 21 can be reset upon sensing of R-waves as indicated by signals from amplifier 24. In accordance with the selected mode of pacing, pacer timing unit 21 triggers generation of pacing pulses by pacer output circuitry 28, as long as rate control unit 26 does not determine that such pulses should not be allowed, consistent with the rate control techniques described herein. Pacer output circuitry 28 is coupled to electrode 22 for delivery of pacing pulses.

Control unit 25 may comprise an interrupt driven microprocessor, and is responsive to interrupts from pacer timing unit 21 identifying the occurrence of sensed R-waves, or the like. The interrupts may be provided from pacer timing unit 21 to control unit 25 via a data/address bus 27. Any necessary mathematical calculations to be performed by control unit 25 and any updating of the values or intervals controlled by pacer timing unit 21 can take place following such interrupts.

Although not illustrated in FIG. 2, system 20 may also include cardioversion or defibrillation functionality. For example, in response to the detection of atrial or ventricular fibrillation or tachyarrhythmia requiring a cardioversion pulse, control unit 25 may activate cardioversion/defibrillation circuitry (not shown), which initiates charging of the high voltage capacitors (not shown). Thereafter, timing of the delivery of the defibrillation or cardioversion pulse may be controlled by pacer timing unit 21.

Figure 3:
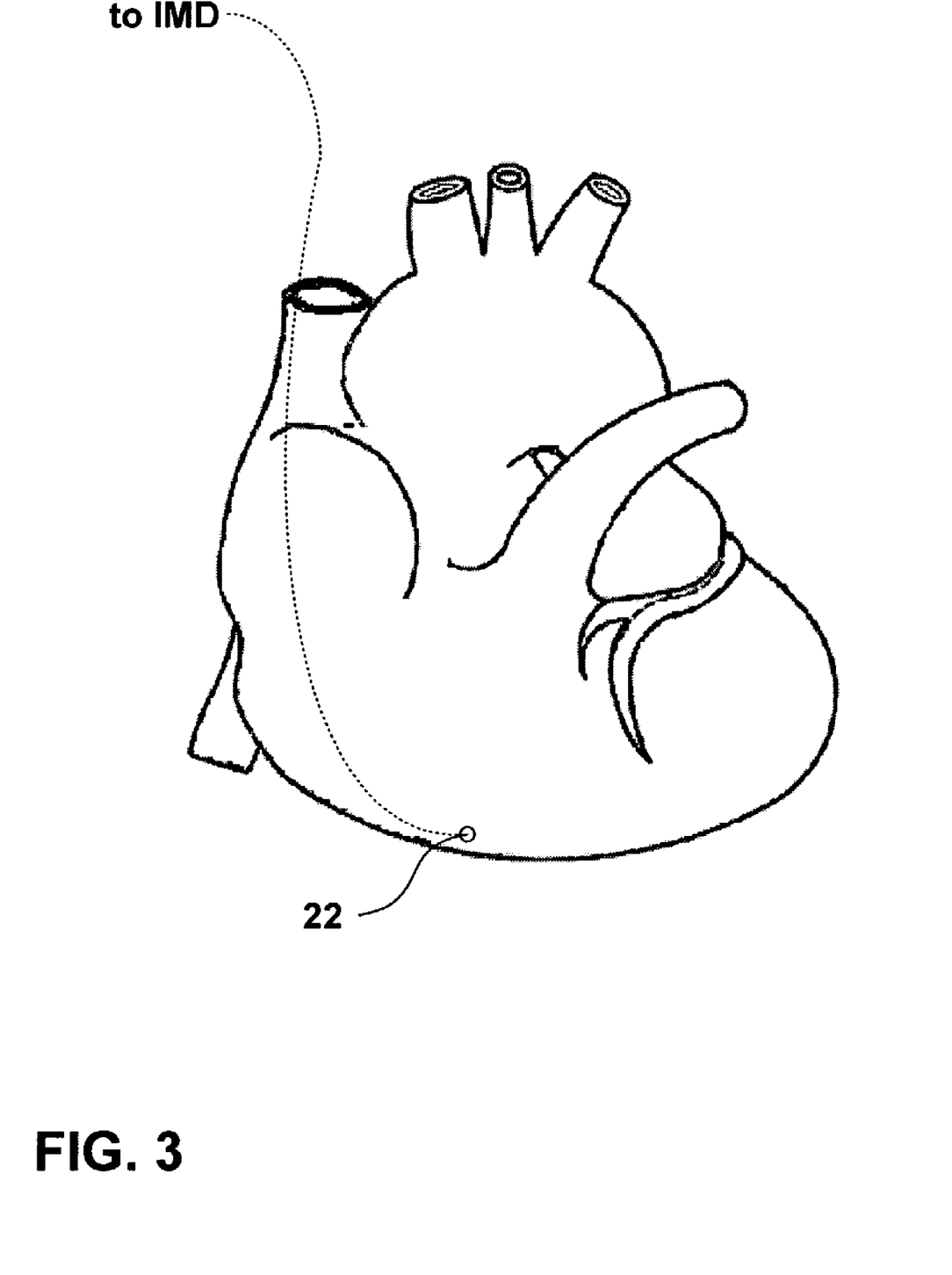
FIG. 3 is a conceptual view of an electrode implanted in a heart in proximity to a ventricle of the heart.

Amplifier 24 is coupled to electrode 22, which represents conceptually a unipolar or bipolar electrode configuration positioned in a patient's ventricle, e.g., as illustrated in FIG. 3. A signal may be generated by amplifier 24 whenever the signal sensed by electrode 22 exceeds a sensing threshold. Pacer timing unit 21 triggers generation of pacing pulses by pacer output circuitry 28, which is coupled to electrode 22.

In accordance with the invention, however, system 20 includes rate control unit 26 that limits the ability of pacer timing unit 21 to trigger generation of pacing pulses by pacer output circuitry 28. In other words, rate control unit 26 only allows pacing pulses to be triggered when the timing of those pacing pulses does not violate the rate control algorithm executed by rate control unit 26. Rate control unit 26 can be integrated as part of pacer timing unit 21, or may be a separate independent unit. Pacer timing unit 21 and rate control unit 26 may comprise hardware, firmware, or possibly software executing on a processing unit such as a microprocessor. If executed in software, pacer timing unit 21 and rate control unit 26 may comprise computer readable instructions stored on a computer readable medium (not shown) and executed in a processing unit.

In any event, rate control unit 26 makes use of a plurality of timing intervals to improve rate control and allow "double-pacing" pulses to be delivered in certain instances, such as when the first pacing pulse does not achieve capture or when double-pacing pulses are applied for cardiac resynchronization. Conventionally, rate controls limit ventricular pacing to approximately one pacing pulse every 300 milliseconds, in order to ensure that ventricular pacing never exceeds 200 paces per minute. Conventionally, ventricular pacing at rates exceeding 200 paces per minute is considered dangerous.

In accordance with the invention, however, rate control unit 26 defines a time interval, referred to herein as a double-pace window, during which another ventricular pace can be delivered without being counted towards the rate limit. In this example of FIGS. 2 and 3, the second ventricular pace may be provided at the same electrode 22 which provided the first ventricular pace. In other examples, however, the second ventricular pace may be provided to a different electrode positioned in the same ventricle, or a different electrode positioned in the other ventricle. In any case, rate control unit 26 defines a first time interval (the double-pace window) that spans approximately 100 milliseconds or less relative to delivery of the first pacing pulse. In addition, rate control unit 26 defines a second timing interval, referred to as a rate control window, that spans approximately 300 milliseconds relative to the first pacing pulse.

A second pulse, i.e., a "double-pacing" pulse, may be delivered by pacer output circuitry 28 within the first time interval in order to achieve capture or for cardiac resynchronization. However, rate control unit 26 does not allow the second pulse to be delivered once the first time interval has elapsed, if the second time interval has not also elapsed. In other words, if pacer timing unit 21 requests delivery of a second pacing pulse, rate control unit 26 only allows pacer output circuitry 28 to deliver the pulse during the first time interval, e.g., within 100 milliseconds of the first pacing pulse. After the first time interval elapses, rate control unit 26 does not allow pacer output circuitry 28 to deliver additional pulses until the second time interval elapses. Once the second time interval elapses, the process can repeat.

For example, if the first interval is 100 milliseconds and the second interval is 300 milliseconds, rate control unit 26 allows pacer output circuitry 28 to deliver a second "double pacing" pulse only when the second pulse occurs within 100 milliseconds of the first pulse. In that case, the second pulse is not allowed after the 100 milliseconds have elapsed and before 300 milliseconds have elapsed. In other words, rate control unit 26 does not allow pacer output circuitry 28 to deliver the second pulse between 100 and 300 milliseconds of the first pacing pulse. The period between 100 and 300 milliseconds of the first pacing pulse can be referred to as a vulnerable period during which delivery of pacing pulses could invoke fibrillation or possibly death. Once the 300 milliseconds have elapsed, rate control unit 26 allows any pacing pulse and the process can repeat.

If the second pulse, i.e. the "double pacing" pulse, is allowed by rate control unit 26 and delivered by pacer output circuitry 28 during the first time interval, then rate control unit 26 restarts the second time interval relative to the second pulse. In that case, rate control unit 26 will block delivery of another pulse until the restarted second time interval has elapsed. For example, if the first interval is 100 milliseconds and the second interval is 300 milliseconds, and a second "double pacing" pulse is delivered within the 100 milliseconds of the first pulse, then rate control unit 26 restarts the second interval of 300 milliseconds relative to delivery of the second pacing pulse. Thus, rate control unit 26 does not allow additional pacing pulses for 300 milliseconds following delivery of the second pacing pulse. Alternatively, in other embodiments, rate control unit 26 may define additional "triple-pacing" pulse windows, or the like.

Figure 4:
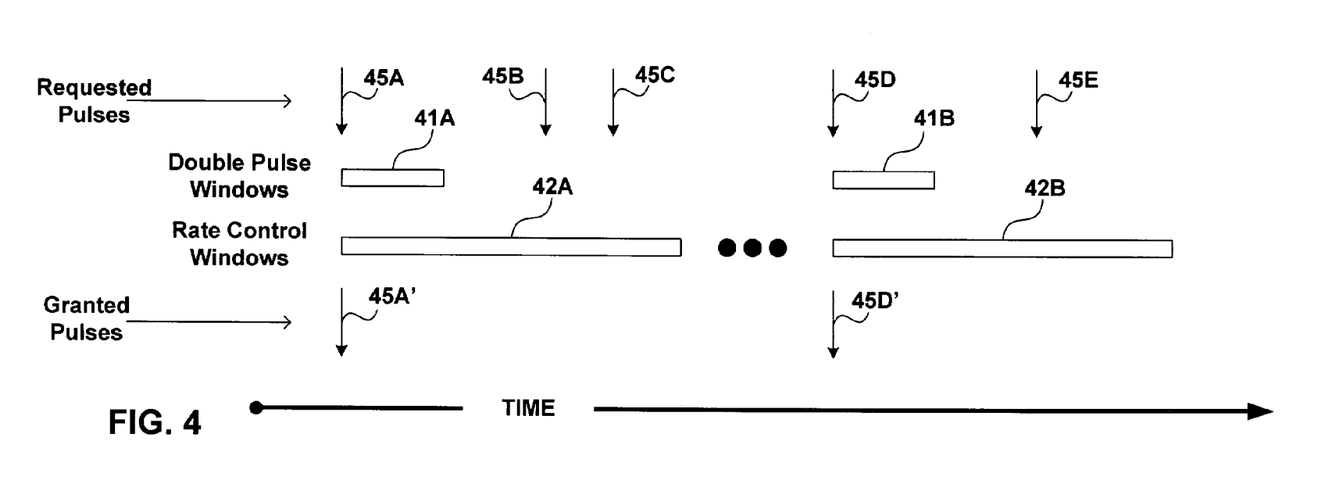
FIGS. 4 and 5 are timing diagrams illustrating rate-controlled pacing techniques according to an embodiment of the invention.
Figure 5:
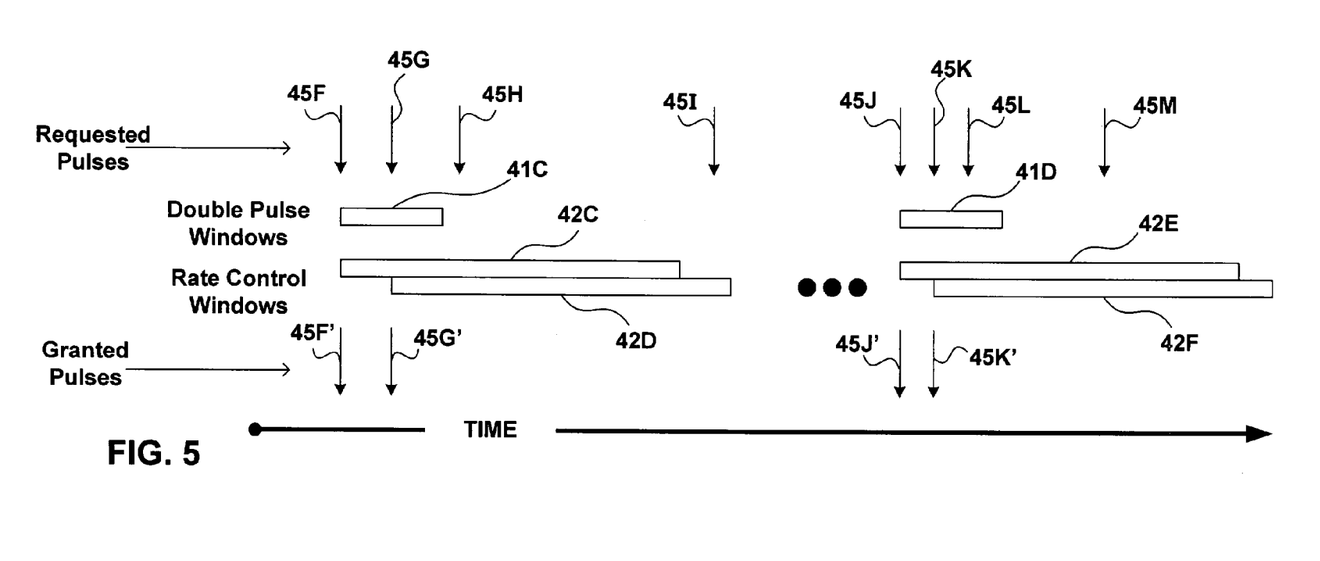

FIGS. 4 and 5 are timing diagrams illustrating techniques implemented by rate control unit 26 (FIG. 2). Rate control unit 26 defines a plurality of timing intervals. Specifically, rate control unit 26 defines first intervals 41A, 41B, 41C and 41D (referred to as double pace windows) and second intervals 42A, 42B, 42C, 42D, 42E, 42F (referred to as rate control windows). Rate control unit 26 receives requested pulses 45A-45M from pacer timing unit 21, and based on the timing of the requested pulses relative to the respective intervals 41, 42, rate control unit 26 either grants or denies the pulse. If granted, pacer output circuitry 28 delivers the pulse to electrode 22.

For example, as shown in FIG. 4 pacer timing unit 21 requests a first pulse 45A and rate control unit 26 grants pulse 45A'. Upon granting pulse 45A', rate control unit 26 defines first interval 41A and second interval 42A. The length of the respective intervals are generally subject to a wide variety of implementation-specific values. However, double pace windows defined by first intervals 41 are shorter than rate control windows defined by second intervals 42. By way of example, first intervals 41 may span approximately 100 milliseconds or less, whereas second intervals 42 may span approximately 300 milliseconds.

As further shown in FIG. 4, requested pulses 45B and 45C by pacer timing unit 21 are not granted by rate control unit 26 because pulses 45B and 45C are requested following first interval 41A and within second interval 42A. The next requested pulse 45D by pacer timing unit 21 is granted by rate control unit 26 as pulse 45D' because second interval 42A has elapsed. At that point, new intervals, e.g., first interval 41B and second interval 42B are defined. Requested pulses 45E by pacer timing unit 21 is not granted by rate control unit 26 because pulse 45E is requested following first interval 41B and within second interval 42B.

As shown in FIG. 5, pacer timing unit 21 requests first pulse 45F and rate control unit 26 grants the first pulse 45F'. Upon granting pulse 45F', rate control unit 26 defines first interval 41C and second interval 42C. Pacer timing unit 21 requests second pulse 45G, and rate control unit 26 grants the second pulse 45G' because it was requested within first interval 41C. At that point, rate control unit 26 redefines the second interval as interval 42D, e.g., spanning approximately 300 milliseconds from delivery of second pulse 45G'. Requested pulses 45H and 45I by pacer timing unit 21 are not granted by rate control unit 26 because pulses 45H and 45I are requested following delivery of second pulse 45G' and within the redefined second interval 42D.

As further shown in FIG. 5, in a subsequent pacing interval, pacer timing unit 21 requests first pulse 45J and rate control unit 26 grants the first pulse 45J'. Upon granting pulse 45J', rate control unit 26 defines first interval 41D and second interval 42E. Pacer timing unit 21 requests second pulse 45K, and rate control unit 26 grants the second pulse 45K' because it was requested within first interval 41D. At that point, rate control unit 26 redefines the second interval as interval 42F, e.g., spanning approximately 300 milliseconds from delivery of second pulse 45K'. Subsequent requested pulses 45L and 45M by pacer timing unit 21 are not granted by rate control unit 26 because pulses 45L and 45M are requested following delivery of second pulse 45K' and within the redefined second interval 42F.

Again, by way of example, first intervals 41 may span approximately 100 milliseconds or less, whereas second intervals 42 may span approximately 300 milliseconds. However, these values are subject to implementation specific lengths. Moreover, the values of first intervals 41 and second intervals 42 may be programmable. Fixed intervals, i.e., non-programmable values for intervals 41 and 42 may be safer, however, avoiding the possibility for abuse by a physician that does the programming. For example, if the values for intervals 41 and 42 were made programmable, improper programming could be dangerous or even lethal to a patient. For this reason, fixed intervals, i.e., non-programmable values, for intervals 41 and 42 are generally preferred, although the invention is not limited in that respect.

The rate control techniques described herein for ventricular pacing may have at least three different applications. The first application involves delivery of a second "double pacing" pulse to the same electrode that delivered the first pacing pulse. For example, if the first pacing pulse did not result in capture of the heart, a second pacing pulse may be delivered to the same location within the first interval. In that case, the second pacing pulse may be delivered at a higher voltage than the first, to better ensure capture. FIGS. 2 and 3 illustrate such an application.

Another application involves delivery of a second "double pacing" pulse to the same ventricle, but via a different electrode than that which delivered the first pacing pulse. In that case, if the first pacing pulse did not result in capture of the heart, a second pacing pulse may be delivered to a different location of the same ventricle within the first interval. Again, the second pacing pulse may be delivered at a higher voltage than the first, to better ensure capture.

Another application involves delivery of a second "double pacing" pulse to a different ventricle via a different electrode than that which delivered the first pacing pulse. In that case, the first and second pacing pulses may be delivered in synchronization within the first time interval in order to resynchronize the heart. In other words, the invention may be used in bi-ventricular cardiac resynchronization applications, ensuring that the first and second pacing pulses are delivered to the respective ventricles within the first time interval, e.g., within 100 milliseconds of one another.

FIG. 6 is another block diagram of an exemplary IPG system 60 in the form a cardiac pacemaker, which may correspond to system 10 of FIG. 1. System 60 is very similar to system 20 of FIG. 2, and includes pacer timing and control unit 68, control unit 70 such as a microprocessor, and rate control unit 72 to limit delivery of pacing pulses as described herein. In this example, system 60 includes two or more amplifiers 64, 66, two or more pacer output circuits 74, 76, and two or more electrodes 62, 63 positioned for delivery of pacing pulses to different locations in the patient. In general, the invention may be modified to include any number of electrodes, and thus any number of amplifiers that provide signals to pacer timing unit 68. Any number of pacing output circuitries may also be employed to generate pacing pulses to the respective electrodes.

Figure 7:
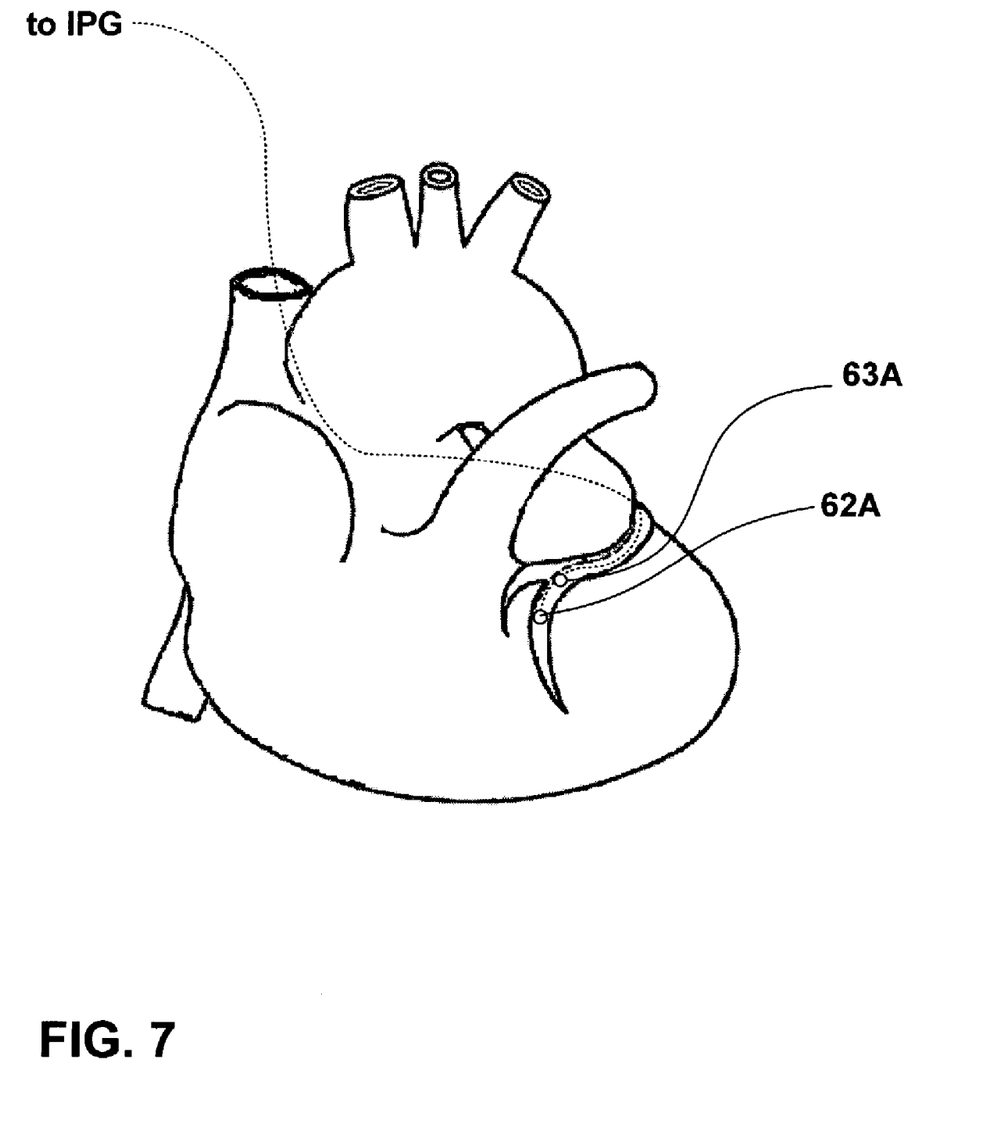
FIG. 7 is a conceptual view of two electrodes implanted in a heart in proximity to a ventricle of the heart.

As illustrated in FIG. 7, electrodes 62 and 63 of FIG. 6 may correspond to electrodes 62A and 63A positioned relative to the same ventricle (in this case the left ventricle). If the first pacing pulse to electrode 62A did not result in capture of the heart, a second pacing pulse may be delivered to electrode 63A within the first interval. In some cases, the second pacing pulse may be delivered to electrode 63A at a higher voltage than the first pacing pulse to electrode 62A, to better ensure capture. Electrodes 62 and 63 may be disposed along the same lead as illustrated in FIG. 7, or may be disposed along different leads.

Figure 8:
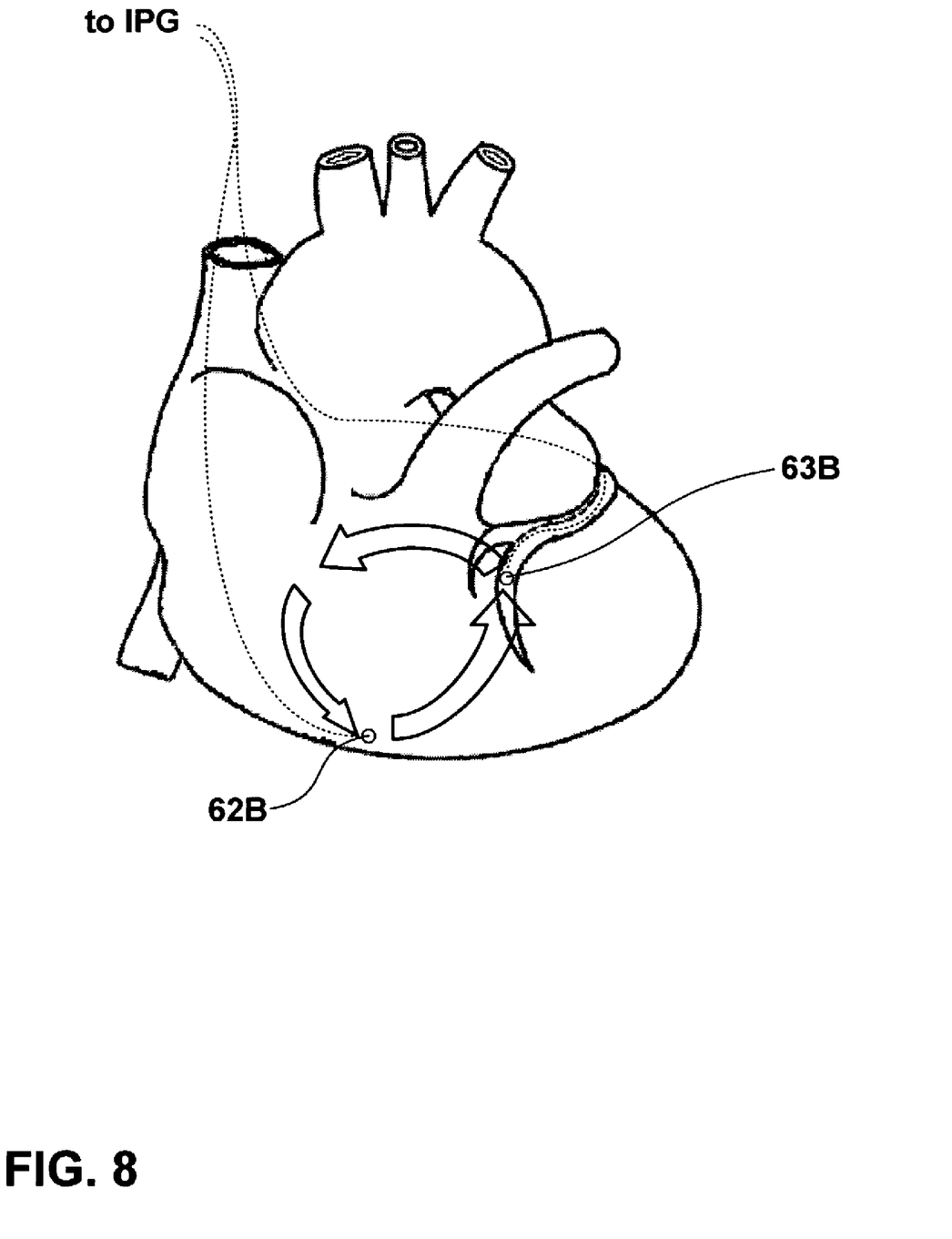
FIG. 8 is a conceptual view of two electrodes implanted in a heart relative to the right and left ventricles of the heart.

As illustrated in FIG. 8, electrodes 62 and 63 of FIG. 6 may correspond to electrodes 62B and 63B positioned relative to different ventricles. Typically electrodes 62B and 63B are disposed along different leads. In any case, the first and second pacing pulses may be delivered in synchronization within the first time interval in order to resynchronize the heart. In other words, the first pacing pulse can be delivered to electrode 62B in the right ventricle of the heart, and the second pacing pulse can be delivered to electrode 63B adjacent left ventricle of the heart, or vice versa. In the example of FIGS. 6 and 8, the invention can achieve bi-ventricular cardiac resynchronization, ensuring that the first and second pacing pulses are delivered to the respective ventricles within the first time interval, e.g., within 100 milliseconds of one another.

A number of embodiments of the invention have been described. However, one skilled in the art will appreciate that the invention can be practiced with embodiments other than those disclosed. For example, although various details of the invention have been provided in the context of cardiac pacing, the same principles may be applied in other implantable pulse generator systems. Also, although many details have been provided in the context of ventricular pacing, the same or similar techniques can be used to rate control atrial pacing or the delivery of stimulation to any cardiac tissue.

The various components of system 20 (FIG. 2) or system 60 (FIG. 6), such as pacer timing unit 21, 68, control unit 25, 70 and rate control unit 26, 72 may be implemented in hardware, software, firmware, or the like. Moreover, one or more of the components may be integrated into a single unit. Example hardware implementations of such components include implementations within an application specific integrated circuit (ASIC), a field programmable gate array (FPGA), a programmable logic device, specifically designed hardware components, one or more processors, or any combination thereof. If implemented in software, a computer readable medium may store computer readable instructions, e.g., program code, that can be executed by a processor or DSP to carry out one of more of the techniques described above. For example, the computer readable medium may comprise random access memory (RAM), read-only memory (ROM), non-volatile random access memory (NVRAM), electrically erasable programmable read-only memory (EEPROM), flash memory, or the like. The computer readable medium may comprise computer readable instructions that when executed in an IPG, carry out one or more of the techniques described herein. The disclosed embodiments are presented for purposes of illustration and not limitation, and The invention is limited only by the claims that follow.

What is claimed is:

1. An implantable pulse generator system comprising an implantable pulse generator device and one or more implantable leads coupled to the implantable pulse generator device to position one or more electrodes within a patient, the system including:
    output circuitry to deliver therapeutic pulses to the patient via the electrodes;
    a timing unit to request the delivery of therapeutic pulses by the output circuitry upon expiration of escape intervals;
    a timing control unit to provide determine and control the escape intervals to provide a pacing rate and to provide for a maximum pacing rate;
    a rate control unit to define first and second rate control time intervals relative to a first stimulation pulse delivered to the patient in a first cardiac chamber at the pacing rate determined by the timing control unit and wherein a timing of the first stimulation pulse is applied to the timing control unit in controlling in the pacing rate, the first time interval being shorter than the second time interval,
    wherein the rate control unit allows delivery of a second stimulation pulse to the first cardiac chamber without applying the timing of the second stimulation pulse to the timing control unit to control the pacing rate when the second stimulation pulse is requested to be delivered at a time during the first time interval, disallows delivery of the second stimulation pulse to the first cardiac chamber when the second stimulation pulse is requested to be delivered at a time following the first time interval during the second time interval, and allows delivery of the second stimulation pulse to the first cardiac chamber when the second stimulation pulse is requested to be delivered at a time subsequent to the second time interval.

2. The implantable pulse generator system of claim 1, further comprising a control unit coupled to the timing unit to define the delivery of therapeutic pulses according to a pacing algorithm.

3. The implantable pulse generator system of claim 1, wherein rate control unit redefines the second time interval relative to the second stimulation pulse in response to allowing delivery of the second stimulation pulse during the first time interval, disallows delivery of a third stimulation pulse when the third stimulation pulse is requested to be delivered at a time during the redefined second time interval, and allows delivery of the third stimulation pulse when the third stimulation pulse is requested to be delivered at a time subsequent to the redefined second time interval.

4. The implantable pulse generator system of claim 1, wherein the implantable leads position the one or more electrodes in a ventricle of the patient, wherein the first and second stimulation pulses are delivered to the ventricle.

5. The implantable pulse generator system of claim 1, wherein a first implantable lead positions a first electrode in one ventricle of the patient for delivery of the first stimulation pulse, and a second implantable lead positions a second electrode in another ventricle of the patient.

6. The implantable pulse generator system of claim 1, wherein the second time interval is approximately 300 milliseconds, and the first time interval is less than or equal to approximately 100 milliseconds.

7. The implantable pulse generator system of claim 1, wherein the implantable pulse generator device comprises a pacemaker, and the one or more implantable leads comprise cardiac leads.

8. A method comprising:
delivering a first stimulation pulse to a first cardiac chamber;
setting an escape interval based upon delivery of the first stimulation pulse wherein the escape interval defines a pacing rate and the pacing rate is precluded from exceeding an upper rate limit;
defining and concurrently initiating first and second rate control time intervals relative to the first stimulation pulse, the first time interval being shorter than the second time interval;
requesting delivery of a second stimulation pulse to the first cardiac chamber subsequent to the first stimulation pulse that does not reset the escape interval so that a timing of the second stimulation pulse does not affect the calculated pacing rate and is not limited by the upper rate limit;
allowing delivery of the second stimulation pulse when the second stimulation pulse is requested to be delivered at a time during the first time interval;
disallowing delivery of the second stimulation pulse when the second stimulation pulse is requested to be delivered at a time following an expiration of the first time interval but during the second time interval; and
allowing delivery of the second stimulation pulse when the second stimulation pulse is requested to be delivered at a time subsequent to an expiration the second time interval.

9. The method of claim 8, further comprising:
redefining the second time interval relative to the second stimulation pulse in response to allowing delivery of the second stimulation pulse during the first time interval;
requesting delivery of a third stimulation pulse subsequent to the allowed second stimulation pulse;
disallowing delivery of the third stimulation pulse when the third stimulation pulse is requested to be delivered during the redefined second time interval; and
allowing delivery of the third stimulation pulse when the third stimulation pulse is requested to be delivered subsequent to the redefined second time interval.

10. The method of claim 9, further comprising delivering the first stimulation pulse to a ventricle of the patient and delivering the second stimulation pulse to the ventricle.

11. The method of claim 10, further comprising delivering the first and second stimulation pulses via an electrode electrically coupled to an implantable pulse generator (IPG).

12. The method of claim 10, further comprising delivering the first stimulation pulse via an electrode electrically coupled to an implantable pulse generator, and delivering the second stimulation pulse via another electrode electrically coupled to the implantable pulse generator.

13. The method of claim 8, wherein the second time interval is approximately 300 milliseconds, and the first time interval is less than or equal to approximately 100 milliseconds.

* * * * *